United States Patent [19]

Ogawa et al.

[11] Patent Number: 4,668,813

[45] Date of Patent: May 26, 1987

[54] METHOD FOR OBTAINING PHYTIN

[75] Inventors: Hiroshi Ogawa, Suzuka; Tomoei Kanno, Okegawa, both of Japan

[73] Assignees: Showa Sangyo Co., Ltd., Tokyo; Shikishima Starch Manufacturing Co., Ltd., Suzuka, both of Japan

[21] Appl. No.: 832,239

[22] Filed: Feb. 24, 1986

[51] Int. Cl.$^4$ ............................................. C07F 9/117
[52] U.S. Cl. ..................................................... 558/147
[58] Field of Search ................................. 558/147, 833

[56] References Cited

U.S. PATENT DOCUMENTS 2,112,553  3/1938  Bartow et al. ....................... 568/833
3,410,929 11/1968  Ledding et al. ...................... 558/147

Primary Examiner—Anton H. Sutto
Attorney, Agent, or Firm—Oblon, Fisher, Spivak, McClelland & Maier

[57] ABSTRACT

A phytin-containing solution such as corn steep liquor, acid extract of rice bran is treated with an anion exchange resin with phytin adsorption. The phytin is then separated from the resin by alkali-elution, then the phytin thus recovered is further subjected to the treatment of hydrolysis under pressure, phosphate removement, purifying, etc. to prepare inositol. Alternatively, the recovered phytin is further subjected to the treatment of desalting, purfiying, etc. to prepare phytic acid.

9 Claims, No Drawings

METHOD FOR OBTAINING PHYTIN

BACKGROUND OF THE INVENTION

1. Field of the Invention

This invention relates to a method for preparing phytin and related products including inositol and phytic acid.

2. Discussion of the Background

Phytin is a calcium magnesium salt of phytic acid. It is distributed in almost all parts of plant tissue, especially in seeds. It is an important source for producing inositol or phytic acid, both of which are used in the food industry. Phytic acid is a hexaphosphoric acid ester of inositol. It has a chelating action by which trace metals in foodstuffs are inactivated, preventing the discoloration and deterioration of foodstuffs.

Inositol is also called mesoinositol or myoinositol. It is contained in plants as a component of phytin, and is found in the free state in animal tissues such as muscle, heart, liver, etc. Inositol is also a component of phosphatides which is widely distributed in natural organisms, especially in mammalian liver and brain, egg yoke, soybean and wheat germ. It is important as a vitamin in the higher animals and performs an important role in the metabolism of fats and cholesterol. A number of studies have shown its lipotropic function, and its effect on cirrhotic livers and hyper-cholesteremia. Inositol has therefore recently become an important substance in the field of health foods in the United States and the other countries.

Inositol is usually produced from raw materials such as rice bran or corn steep liquor. For example, rice bran may be treated with an organic or inorganic acid to extract phytin. Phytin is then precipitated and separated from the extract, usually by filtration, to remove unwanted proteins and carbohydrates. The separated phytin is then hydrolyzed under pressure to recover inositol, which is further purified, concentrated, and crystallized. In this method, organic solvents, water-soluble metallic salts such as iron chloride, manganese sulfate, and water-soluble alkaline substances such as sodium hydroxide, aqueous ammonia, may be employed as precipitants for phytin. However, phytin usually precipitates as a colloidal, pasty substance when these precipitants are used, rendering satisfactory elimination of impurities extremely difficult.

Phytin may also be precipitated with calcium compounds such as calcium phytate. However in this case a large amount of proteinous, difficult to remove, impurities co-precipitate. Calcium phytate itself precipitates as a pasty crystallized mass. This often causes process problems, such as blocking of the nozzles of centrifugal separator during the operation. And a large amount of fine crystallized calcium phosphate forms as a by-product after the phytin hydrolysis step. A considerable amount of inositol is thus lost in this crystalline material in the successive inositol-calcium phosphate separating step, resulting in an unavoidable economic disadvantage due to a decrease in inositol recovery. The separated calcium phosphate is also unsatisfactory from an economical viewpoint due to its low purity.

There is thus a strongly felt need for a facile process for the production of phytin and related products in high yields and in high degrees of purity.

SUMMARY OF THE INVENTION

Accordingly, it is an object of this invention to provide a process for producing phytin and related products, e.g. inositol, phytic acid in high yields.

It is another ojbect of this invention to provide a process for producing phytin and related products, having a high degree of purity.

It is another object of this invention to provide a process for the facile production of phytin and related products.

It is another object of this invention to provide an economically advantageous process for the production of phytin and related products, e.g. inositol and phytic acid.

It is another object of this invention to provide a process for the production of pure phytic acid or inositol by further treatment of the phytin obtained.

The present inventors have now surprisingly discovered a novel process which satisfies all of the above objects of this invention, and other objects which will become apparent from the description of the present invention given herein below. In accordance with the invention, phytin is first adsorbed onto an anion exchange resin. It is then separated from the anion exchange resin by alkali elution. This method excludes the phytin precipitation step. The level of impurities contaminating the product is decreased, and the whole process is simplified. High purity phytic acid can be readily obtained from the phytin, using any known treatment method, such as desalting. The phytic acid can be further treated to prepare high purity inositol using any known treatment such as hydrolysis under pressure, separation of phosphates, and purification.

DETAILED DESCRIPTION OF THE PREFERRED EMBODIMENTS

This invention provides a method for preparing high purity phytin in a simplified and an economical process. This invention also provides a method for preparing pure phytic acid and/or inositol by further treatment of the phytin obtained.

Phytin is extracted with organic or inorganic acid in a known manner and under known conditions from a phytin-containing raw material such as rice bran, wheat bran, or corn. Defatted rice bran is a good source for inositol preparation, from which phytin is extracted by 1% aqueous sulfuric acid solution. Corn steep liquor which is a steep water of corn grain in a dilute aqueous sulfur dioxide solution obtained by a corn wet-milling process, is also an acid extraction of phytin. It is a practical source for inositol preparation. It contains phytic acid or its salts in an amount corresponding to 2% (on a dry basis) of inositol.

The phytin-containing solution thus obtained is first contacted with a bed of anion exchange resin which adsorbs the phytin. Anion exchange resins useful for this purpose may be $CO_3$, $CH_3COO$, $Cl$, $SO_3$, $OH$, etc. type resins. Although any resin may be used, some resins vary from each other on the basis of their phytin-adsorbability, selectivity, effect on removing impurities, and the other characteristics. There are some differences between the types of the resin on the yield of phytin and the other effects. Practically speaking, Cl and $SO_3$ type resins are preferable for this purpose. OH type resins are also suitable. Useful commercially available resins are, for example, Amberlite IR-45, IRA-68, IRA-93, IRA-410, and IRA-411, which are produced by ORUGANO Co., Ltd., Daiya-ion; and SA20A, SA21A, WA30, WA40, and WA11, which are produced by NIHON RENSUI Co., Ltd.; and Dowex MSA-1 and MSA-266, which are the produced by DOWEX Co., Ltd.

The conditions for the ion exchange resin treatment are usually selected within the following ranges: temperature =5 to 20° C., pH =1 to 5, concentration of phytin-containing solution =1 to 40% (w/v), flow rate, or space velocity (SV), for ion exchange resin (the amount of liquid fed to the resin per hour/volume of the resin) =0.5 to 20.

Phytin is adsorbed on the ion exchange resin by the above treatment. The resultant resin is then preferably washed preliminarily with hot water (t=30-85° C.). The adsorbed phytin is then separated from the resin by alkaline elution. The alkaline substances which may be used for this purpose can be sodim hydroxide, potassium hydroxide, ammonium hydroxide and mixtures thereof. However the alkaline subtances which can be used are not limited to these particular examples. The elution conditions may vary according to the kind of alkali substance used, the concentration of their aqueous solution, the kind of ion exchange resin used, the properties of the phytin-containing solution, etc. In the case of sodium hydroxide, however, the following conditions are preferable: temperature =room temperature to 70° C.; SV =0.5 to 10; and the pH of the eluted solution maintained between 9 and 12.

The eluted solution thus obtained contains mainly the sodium salt of phytic acid. The impurities in the solution, such as proteins, carbohydrates are present only in very low concentrations. Procedural difficulties in successive steps caused by these impurities are therefore considerably eliminated.

The eluted phytin solution is further subjected to the steps of hydrolysis under pressure, removal of the phosphates, purification concentration, and crystallyzation. Thus, an inositol product of high purity can be obtained with phosphates as a by-product. Sodium secondary phosphate will be obtained as a by-product when sodium hydroxide is used for elution. Alternatively, the eluted phytin solution is desalted by ion exchange resin to produce phytic acid.

By the process described above phytin is separated directly from a phytin-containing solution by a simple adsorption procedure. The troublesome treatment of a colloidal, pasty phytin precipitates found in conventional methods is completely excluded. Nearly all of the impurities remain in the original solution and do not contaminate the separated phytin. Thus, a highly purified inositol product and/or phytic acid product is produced very easily and economically.

Other features of this invention will become apparent from the following description of exemplary embodiments which are given for purposes of illustration, and are not intended to be limiting of the invention. EXAMPLE 1

Comparison of the method of this invention with a conventional inositol preparing process.

Phytin was separated by the methods given below using in each method 20 liters of corn steep liquor, and the inositol recovery and the protein content of the inositol were determined. The corn steep liquor used had pH of 4.1 and a concentration of 7.7%. It contained about 2% inositol.

Inositol recovery was calculated as follows: first an organic phosphor content observed in recovered phytin is calculated into phytic acid ($C_6H_{18}O_{24}P_6$, molecular weight 660) equivalents, and then the phytic acid content thus obtained is calculated into inositol ($C_6H_{12}O_6$, molecular weight 180) equivalents.

(1) Convention method

An aqueous 15% solution of calcium hydroxide was added to the corn steep liquor, adjusting the pH at 6.0 and precipitating phytic acid as its calcium salt. The precipitate was separated by filtration and washed with 1.5 liters of warm water (temperature ca. 50° C.). 249 grams of phytin (as calcium salt), which is equivalent to 34.1 grams of inositol, were obtained.

(2) Method according to the present invention (1)

The corn steep liquor was passed through a bed of anion exchange resin at SV=4 with phytin adsorption. The resin used was 1 liter of OH type IRA-411 (produced by ORUGANO Co., Ltd.) which was regenerated to $CO_3$ type before use.

The phytin-adsorbed bed of resin was washed by 1.5 liters of warm water (temperature ca. 50° C.). Phytin was then eluted from the resin by passing a 7% aqueous sodium hydroxide solution through the bed of resin at SV=1. 115 grams of phytin was recovered as its sodium salt, which is equivalent to 115 grams of inositol (18.8 grams per a liter of resin).

(3) Method according to the present invention (2)

An anion exchange resin identical to that used in the preceding example (2) was regenerated to the $CH_3COO$ type and treated with the corn steep liquor under the conditions used in example (1). 92 grams of phytin was recovered, which is equivalent to 16.5 grams of inositol per a liter of resin.

(4) Method according to the present invention (3)

An anion exchange resin IRA-68 of the OH type (produced by ORUGANO Co., Ltd.) was regenerated to the Cl type and treated with the corn steep liquor under the same conditions used in example (2). 212 grams of phytin was recovered, which is equivalent to 34.8 grams of inositol per a liter of resin.

(6) Method according to the present invention (5)

An anion exchange resin IRA-411 of the OH type was used for phytin recovery under the conditions used in example (2). 106 grams of phytin, which is equivalent to 17.3 grams of inositol per a liter of resin, was obtained.

The results obtained are tabulated below.

TABLE 1

| Method | Yield of crude inositol (%) | Protein content (%) |
|---|---|---|
| Conventional method | 94.2 | 73.5 |
| Method of this invention (1) | 51.9 | 1.7 |
| Method of this invention (2) | 45.6 | 1.4 |
| Method of this invention (3) | 96.1 | 0.8 |
| Method of this invention (4) | 99.2 | 1.2 |
| Method of this invention (5) | 47.8 | 2.1 |

NB (1) Yield of crude inositol:
$$\frac{\text{The amount of inositol converted from the recovered phytin}}{\text{The amount of inositol found in the corn steep liquor}} \times 100 \, (\%)$$

(2) Protein content:
$$\frac{\text{The protein content in recovered phytin}}{\text{The amount of inositol converted from the recovered phytin}} \times 100 \, (\%)$$

As shown in Table 1, the protein content which represents impurities in phytin product is considerably lower in the products obtained by the method of this invention than in the product obtained by the conventional method. An anion exchange resin regenerated to the Cl or $SO_3$ type apparently exhibits especially high yields of phytin recovery, which is shown as the yield of crude inositol in Table 1.

EXAMPLE 2

150 liters of corn steep liquor (3.5 Baume and pH 4.1) containing 2.0 kg/m³ of inositol, calculated from phytin content, was passed through a bed consisting of 7.5 liters of anion exchange resin at SV=4 with phytin adsorption. The resin used was IRA-68 (produced by ORUGANO Co., Ltd.) which was regenerated to the Cl type with hydrochloric acid before use. The phytin-adsorbed resin was washed with a counterflow of warm water, then a 15% aqueous sodium hydroxide solution was passed through the resin at SV=1. About 12 liters of phytin-eluted solution was obtained.

The eluted solution was then concentrated to about 43 to 48% of sodium phytate content which is equivalent to 8.5 to 9.5% of inositol, and the concentrated solution was subjected to hydrolysis under pressure at 180° C. for 3 hours. The resultant hydrolyzate was filtered to remove water-insoluble salts such as calcium phosphates, magnesium phosphates, etc., and the filtrate was subjected to a crystallizing procedure to separate the sodium secondary phosphate contained therein. The resultant inositol-containing solution thus obtained was decolorized and desalted by ion exchange resin and concentrated to around 25% inositol content. Inositol was crystallized out as its salt from the solution active carbon treatment, and some 250 grams of anhydrous inositol (moisture below 0.5%) was obtained by vacuum drying.

The amount of impurities contained in the product was very little.

About 5.6 kg of crystallized sodium secondary phosphate was obtained about 5.6 kg as a by-product in this process.

EXAMPLE 3

10 kg of defatted rice bran was extracted twice with an aqueous solution of sulfuric acid, first with a 1% solution and secondly with a 0.3% solution. The whole extracted solution volume of about 100 liters was treated by the same anion exchange resin used in Example 2 at SV=2.

The phytin adsorbed resin was washed with warm water and eluted with a 10% aqueous solution of sodium hydroxide at SV=1. The recovered sodium phytate solution was about 15 liters, and about 206 grams of refined anhydrous inositol was obtained using the treatment of Example 2.

EXAMPLE 4

A liquid containing 100 ml of 35% hydrochloric acid in 13 liters of corn steep liquor was subjected to treatment with 1 liter of anion exchange resin of the OH type (Amberlite IRA-93) at SV=2.

About 22 grams of refined inositol was obtained by a treatment identical to that of Example 2.

EXAMPLE 5

Eluted solutions of sodium phytate obtained in the same manner as described in Examples 2 and 3 were treated for desalting 4 liters of OH-type cation exchanger (Amberlite IR-120B; DAIYA-ION SK1B and Dowex 88 are also available) at SV=2. The solution was concentrated to about 55% and decolored by active carbon.

1,340 grams of high quality, 50% phytic acid was recovered.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A process for obtaining phytin or a product related to phytin, said process comprising:
    (i) contacting a phytin-containing solution with an anion-exchange resin at a ph of 1–5 for a period of time sufficient for adsorption of at least part of the said phytin onto the said anion-exchange resin; and
    (ii) eluting phytin from the said anion-exchange resin.
2. The process of claim 1, said process comprising:
    (iii) recovering the said phytin from the eluate.
3. The process of claim 2, said process comprising:
    (iv) desalting and purifying the recovered phytin to obtain phytic acid.
4. The process of claim 1, comprising using a $CO_3$, a $CH_3COO$, a Cl, a $SO_3$ or a OH-type resin.
5. The process of claim 1, comprising using a temperature of from 5 to 20° C. in step (i).
6. The process of claim 1, comprising using a phytin-containing solution having a phytin concentration of from 1 to 40% in step (i).
7. The process of claim 1, comprising washing the anion resin containing adsorbed phytin with hot water prior to step (ii).
8. The process of claim 1, comprising eluting the said phytin with a alkaline elution media.
9. The process of claim 8, comprising using sodium hydroxide, potassium hydroxide ammonium, hydroxide or a mixture thereof.

* * * * *

UNITED STATES PATENT AND TRADEMARK OFFICE
CERTIFICATE OF CORRECTION

PATENT NO. : 4,668,813
DATED : MAY 26, 1987
INVENTOR(S) : HIROSHI OGAWA; TOMOEI KANNO

It is certified that error appears in the above-identified patent and that said Letters Patent is hereby corrected as shown below:

<u>COL.</u>   <u>LINE</u>

ABSTRACT   Last Line, delete "purfiying" and insert --purifying--,
2          6, delete "ojbect" and insert --object--,
3          4, delete "the",
           18, delete "sodim" and insert --sodium--,
           20, delete "subtances" and insert --substances--,
           38, delete "crystallyzation" and insert --crystallization--
           47, delete "a",
           57, EXAMPLE 1 should be on one line,
4          5, delete "Convention" and insert --Conventional--,
6          33, delete "ph" and insert --pH--,
           53, delete "a" and insert --an--,
5          44, delete "about 5.6 kg"

Signed and Sealed this

Seventeenth Day of May, 1988

*Attest:*

DONALD J. QUIGG

*Attesting Officer*  *Commissioner of Patents and Trademarks*